(12) United States Patent
Kalkanoglu et al.

(10) Patent No.: US 9,243,409 B2
(45) Date of Patent: Jan. 26, 2016

(54) CONTROLLED TIME-RELEASE ALGAE RESISTANT ROOFING SYSTEM

(71) Applicant: CertainTeed Corporation, Valley Forge, PA (US)

(72) Inventors: Husnu M. Kalkanoglu, Swarthmore, PA (US); Keith C. Hong, Lititz, PA (US); Joong Youn Kim, Newtown Square, PA (US); Ming Liang Shiao, Collegeville, PA (US)

(73) Assignee: CertainTeed Corporation, Malvern, PA (US)

( * ) Notice: Subject to any disclaimer, the term of this patent is extended or adjusted under 35 U.S.C. 154(b) by 0 days.

(21) Appl. No.: 14/468,974

(22) Filed: Aug. 26, 2014

(65) Prior Publication Data

US 2015/0007746 A1  Jan. 8, 2015

Related U.S. Application Data

(63) Continuation of application No. 13/932,983, filed on Jul. 1, 2013, now abandoned, which is a continuation of application No. 11/610,405, filed on Dec. 13, 2006, now abandoned.

(60) Provisional application No. 60/597,903, filed on Dec. 23, 2005.

(51) Int. Cl.
| | |
|---|---|
| *B32B 5/16* | (2006.01) |
| *B05D 7/00* | (2006.01) |
| *E04D 13/00* | (2006.01) |
| *C09C 1/00* | (2006.01) |
| *A01N 25/12* | (2006.01) |
| *A01N 25/26* | (2006.01) |
| *A01N 59/16* | (2006.01) |
| *A01N 59/20* | (2006.01) |
| *C09D 5/14* | (2006.01) |
| *E04D 5/12* | (2006.01) |
| *E04D 1/00* | (2006.01) |

(52) U.S. Cl.
CPC .............. *E04D 13/002* (2013.01); *A01N 25/12* (2013.01); *A01N 25/26* (2013.01); *A01N 59/16* (2013.01); *A01N 59/20* (2013.01); *C09C 1/00* (2013.01); *C09D 5/14* (2013.01); *E04D 1/00* (2013.01); *E04D 5/12* (2013.01); *E04D 2001/005* (2013.01); *Y10T 428/24372* (2015.01); *Y10T 428/2991* (2015.01); *Y10T 428/2993* (2015.01); *Y10T 428/2998* (2015.01); *Y10T 428/31815* (2015.04)

(58) Field of Classification Search
CPC .............. Y10T 428/25; Y10T 428/259; Y10T 428/2991; Y10T 428/2993; Y10T 428/2998; C09C 1/00; C09C 3/063
USPC ........... 428/403–402; 427/213–215, 218, 220
See application file for complete search history.

(56) References Cited

U.S. PATENT DOCUMENTS

| | | | | |
|---|---|---|---|---|
| 3,507,676 | A * | 4/1970 | McMahon | 428/145 |
| 5,356,664 | A * | 10/1994 | Narayan et al. | 428/404 |
| 5,382,475 | A * | 1/1995 | Kayser | 428/403 |
| 6,214,466 | B1 * | 4/2001 | Joedicke | 428/404 |

(Continued)

*Primary Examiner* — Holly Le
(74) *Attorney, Agent, or Firm* — Paul & Paul (57) ABSTRACT

Time-release algae-resistant roofing granules have a base particle including an algaecide and an outer coating layer including another algaecide. The at least two algaecides are released over different predetermined periods. The outer layer protects the base particle from exposure to the environment for a predetermined period, then fails catastrophically so that the interior algaecide can be released.

20 Claims, 3 Drawing Sheets

(56) References Cited

U.S. PATENT DOCUMENTS

| | | | |
|---|---|---|---|
| 2004/0139886 A1* | 7/2004 | Joedicke | 106/287.1 |
| 2006/0251807 A1* | 11/2006 | Hong et al. | 427/212 |
| 2007/0148342 A1* | 6/2007 | Kalkanoglu et al. | 427/212 |
| 2013/0295155 A1* | 11/2013 | Kalkanoglu et al. | 424/419 |

* cited by examiner

CONTROLLED TIME-RELEASE ALGAE RESISTANT ROOFING SYSTEM

CROSS-REFERENCE TO RELATED APPLICATIONS

The present application is a continuation of pending U.S. patent application Ser. No. 13/932,983 filed Jul. 1, 2013, which was a continuation of U.S. patent application Ser. No. 11/610,405, filed Dec. 13, 2006, and claimed the priority of U.S. Provisional Patent Application 60/597,903, filed Dec. 23, 2005.

BACKGROUND OF THE INVENTION

1. Field of the Invention

The present invention relates to asphalt roofing shingles, protective granules for such shingles, and processes for making such granules and shingles.

2. Brief Description of the Prior Art

Pigment-coated mineral rocks are commonly used as color granules in roofing applications to provide aesthetic as well as protective functions to the asphalt shingles. Dark blotches or streaks sometimes appear on the surfaces of asphalt shingles, especially in warmer humid climates, because of the growth of algae and other microorganisms. The predominant species responsible is *Gloeocapsa* sp, a blue-green algae. Other microbial growth, including fungi, moss and lichen, can also occur under proper conditions, for example, in a shady and/or persistently damp environment. In addition to being aesthetically unpleasant, the discoloration can lead to heat buildup and accelerate premature roofing failure. Eventually, severe discoloration of the entire roof can occur.

Various methods have been used in an attempt to remedy the roofing discoloration. Washing the roof surfaces with dilute cleaning solutions containing a strong oxidizer such as bleach can remove the algae from roofs. However, frequent washing and cleaning with cleaning solutions is required, since the effective duration of such treatments is rather short. In addition, topical treatments with organic algaecides have been used. However, such topical treatments are also usually effective only for short term, typically one to two years.

If the freshly cleaned surfaces are treated with a coating containing some form of biocides, the antimicrobial properties could remain for a long period of time, between five to seven years. To prevent algal growth, various types of biocides have been used. The most commonly used biocides are metals and inorganic metal oxides, such as, for example zinc metal granules and copper oxide-coated granules. However, these biocides typically persist for around ten years, and in some limited cases, for periods approaching fifteen years. One drawback is these compounds are effective against only one microbe, *Gloeocapsa* sp. At the same time, the service life of roofing products can extend considerably longer than ten to fifteen years, depending on the composition and structure of the roofing materials employed to construct the roof.

Companies, including Minnesota Mining and Manufacturing (3M) and ISP Mineral Products Inc., have commercialized several algaecide granules that are effective in inhibiting algae growth.

A common method used to prepare algae-resistant (AR) roofing granules generally involves two major steps. In the first step, metal oxides such as cuprous oxide and/or zinc oxide are added to a clay and alkali metal silicate mixture. The mixture in turn is used to coat crushed mineral rocks. The mixture is rendered insoluble on the rock surfaces by firing at high temperatures, such as about 500° C., to provide a ceramic coating. In the second step, the oxides covered rocks are coated with various color pigments to form colored algae-resistant roofing granules. The algae-resistant granules, alone, or in a mixture with conventional granules, are then used in the manufacture of asphalt shingles using conventional techniques. The presence of the algae-resistant granules confers algae-resistance on the shingles.

Roofing granules typically comprise crushed and screened mineral materials, which are subsequently coated with a binder containing one or more coloring pigments, such as suitable metal oxides. The binder can be a soluble alkaline silicate that is subsequently insolubilized by heat or by chemical reaction, such as by reaction between an acidic material and the alkaline silicate, resulting in an insoluble colored coating on the mineral particles.

U.S. Pat. No. 3,507,676 discloses roofing granules containing zinc, zinc oxide, or zinc sulfide, as an algaecide and fungicide.

Algae resistant shingles are disclosed, for example, in U.S. Pat. No. 5,356,664 assigned to Minnesota Mining and Manufacturing Co., which discloses the use of a blend of algae-resistant granules and non-algae-resistant granules. The algae-resistant granules have an inner ceramic coating comprising cuprous oxide and an outer seal coating initially devoid of copper.

There is a continuing need for algae-resistant roofing products having algaecide leaching rates that can be controlled so that the roofing products can be tailored for specific local conditions. In addition, there is a continuing need for algae-resistant roofing products that can provide sustained algae-resistance over extended periods of time.

SUMMARY OF THE INVENTION

The present invention provides algae-resistant roofing granules, algae-resistant sheet roofing products such as asphalt shingles and roofing membranes, and processes for make such products. Algae-resistance is provided by a plurality of antimicrobial agents, which exhibit different release rates over time. In one presently preferred embodiment, degradable boundary or containment layers are used to control the release of biocides.

However, in general, the present invention provides at least a first anti-microbial agent and a second anti-microbial agent, the first anti-microbial agent and the second anti-microbial agent each having characteristic and differing release rates from the algae-resistant roofing granules, such that the different release behavior results in effective algae resistance over a longer period than if only the first anti-microbial agent or the second anti-microbial agent were employed in the absence of the other. The differing release rates can be the result of the physical and/or chemical characteristics of the anti-microbial agents themselves. For example, the first anti-microbial agent may differ in aqueous solubility from the second anti-microbial agent. In addition, or alternatively, the difference in release rates may be related to the physical structure of the algae-resistant granules. For example, the algae-resistant granule may include at least two coating layers. In this case, the first anti-microbial agent may be dispersed in an inner coating layer, with the second anti-microbial agent being dispersed in an outer coating layer, such that the outer coating layer(s) inhibits the diffusion of the first anti-microbial agent from the algae-resistant granules. The outer coating layer(s) can include, for example, a layer of a degradable material, that fails catastrophically after a predetermined period. Such a structure, or interlayer, can provide for an induction period before the first algae-resistant agent is effectively released from the algae-resistant granules. During the induction period for release of the first anti-microbial agent, the second anti-microbial agent can be diffusing out from an outer layer of the granule, thus providing interim algae resistance.

In one presently preferred embodiment of the present invention, the algae-resistant sheet roofing products include algae-resistant roofing granules.

The present invention provides a process for producing time-release algae-resistant roofing granules. This process comprises providing base particles comprising at least one first algaecidal material. As disclosed below, the base particles can be prepared in a number of different ways. The base particles are in turn encapsulated with an outer coating composition including at least one second algaecidal material to form an outer layer. The at least one second algaecidal material preferably differs from the at least one first algaecidal material. The encapsulating outer layer protects the base particles from exposure to the environment. The outer coating composition is preferably selected such that the outer layer fails catastrophically after a predetermined period thereby exposing the base particles to the environment. In the interim, during the predetermined period, the at least one second algaecidal material is releasable from the outer layer, thereby providing algae resistance. After the outer layer fails, the base particle is exposed to the environment, and the at least one first algaecidal material thereafter provides algae resistance.

In one presently preferred embodiment, the base particles are prepared by providing inert core particles, and subsequently forming the base particles by coating the inert core particles with an inner coating composition to form an inner layer on the inert core particles. In this case, the inner coating composition preferably includes the at least one first algaecidal material.

Preferably, the inner coating composition includes a binder, which preferably comprises an aluminosilicate material, such as clay, and an alkali metal silicate. The inner coating composition can also include colorants, or solar reflective additives, such as metal oxide pigments.

In the present process, the at least one first algaecidal material of the inner coating composition is preferably selected from the group consisting of compounds and/or zinc compounds, and mixtures thereof, with cuprous oxide and zinc oxide being especially preferred. When cuprous oxide is employed as the at least one first algaecidal material, the cuprous oxide preferably comprises at least 0.5 percent of the algae-resistant granules. When zinc oxide is employed as the at least one first algaecidal material, the zinc oxide preferably comprises at least 0.05 percent by weight of the algae-resistant granules.

In another presently preferred embodiment of the present process, the base particles are prepared by providing a metallic or metal oxide granule core, such as zinc granules or copper oxide granules. In this case, the at least one first algaecidal material is preferably selected from the group consisting of zinc, copper and copper oxide.

In another presently preferred embodiment of the present process, the base particles are prepared by providing the at least one first algaecidal material, and forming the base particles by encapsulating the at least one first algaecidal material in microshells. Each microshell has a wall enclosing an interior cavity, and the interior cavity contains the at least one first algaecidal material. Preferably, the microshell wall is at least partially permeable to the at least one first algaecidal material.

In a presently preferred embodiment of the process of the present invention, the process further comprises providing an interlayer on the base particles. The interlayer preferably enhances the release of the at least one second algaecidal material under predetermined conditions. In one aspect of the process of the present invention, the interlayer preferably includes a water-swellable resin. Preferably, the water-swellable resin is selected from the group consisting of natural or synthetic water-swellable resins, starch, cellulose, and gums. In another aspect of the process of the present invention, the interlayer preferably includes a UV degradable material. Optionally, a photocatalytic material, such as, for example, the anatase form of titanium oxide, can also be added to modify material degradation. Preferably, the UV degradable polymeric material is selected from the group consisting of virgin and recycled polyolefins and polyolefin copolymers, and combinations thereof. In a further aspect of the process of the present invention, the at least one first algaecidal material releases algaecidal metal ions, and the interlayer includes at least one metal oxidizable by the algaecidal metal ions. Preferably, in this case the at least one first algaecidal material releases copper ions, and the interlayer includes zinc.

Preferably, in the present process, the outer coating composition includes a binder. Preferably, the composition and/or morphology of the encapsulating outer layer are selected such that the encapsulating outer layer fails after a predetermined time to expose the first layer to the environment. Thus, the second algaecide is released from the outer layer during the initial predetermined period.

In one presently preferred embodiment, the binder of the outer coating composition comprises an organic polymeric material. The organic polymeric material is preferably selected from the group consisting of poly(meth)acrylates, polyurethanes and polyureas; and the inorganic material is an aluminosilicate or phosphate material. In the process of the present invention, the at least one second algaecidal material is preferably initially uniformly dispersed in the organic polymeric material. The second algaecidal material subsequently diffuses to the exterior surface of the outer layer and is released into the environment.

In another presently preferred embodiment, the binder of the outer coating composition comprises an inorganic material. The inorganic polymeric material is preferably selected from the group consisting of aluminosilicate, silica and phosphate materials. Silica materials may be derived, for example, from sol-gel chemistries or colloidal silica dispersions or suspensions, or the like. In the process of the present invention, the at least one second algaecidal material is preferably initially uniformly dispersed in the inorganic material. The second algaecidal material subsequently diffuses to the exterior surface of the outer layer and is released into the environment.

In a presently preferred embodiment, the at least one second algaecidal material is a quaternary ammonium compound. Preferably, the quaternary ammonium compound is selected from the group consisting of n-alkyl dimethyl benzyl ammonium chloride, dimethyl didecyl ammonium chloride, and poly(oxy-1,2-ethanediyl(dimethylimino)-1,2-ethanediyl (dimethylimino)-1,2-ethanediyl dichloride). In some instances it may be desirable to employ a quaternary ammonium functionality bound to an organic polymer structure. In a preferred such material, the organic polymeric material is a poly(meth)acrylate including at least one quaternary ammonium salt functional group. Other polymer backbone structures could also be employed.

In a presently preferred embodiment, the at least one second algaecidal material is an organic biocide compound. Preferably, the organic biocide can include one or more compounds that are halogen based, nitrogen based, sulfur based, or phenolics. An exemplary halogen based organic biocide is 3-iodo-2-propynylbutyl carbamate (IPBC). Oxazolidine compounds are representative of nitrogen based biocides. An exemplary sulfur based organic biocide is 2-n-octyl-4-isothiazolin-3-one (OIT). An example of a phenolic organic biocide is trichlorophenoxy phenol (TCPP).

Preferably, the outer layer has a thickness of from about 5 micrometers to about 200 micrometers, and more preferably the outer layer has a thickness of from about 12.5 micrometers to about 40 micrometers.

The present invention also provides time-release algae-resistant roofing granules. Each such granule comprises a base particle that includes at least one first algaecidal material. The base particles are encapsulated with an outer coating composition that forms an outer layer and which includes at least one second algaecidal material. Preferably, the at least one second algaecidal material differs from the at least one first algaecidal material. The at least one second algaecidal material provides algae-resistance during an initial predetermined period. During this initial predetermined period, the outer layer encapsulating the base particles preferably protects the base particles from substantial exposure to the environment. The composition and/or the morphology of the outer coating layer is preferably selected so that the outer layer fails catastrophically after the initial predetermined period, thereby exposing the base particle to the environment. After the failure of the outer layer, the base particle is exposed to the environment, and the at least one first algaecidal material thereafter provides algae resistance.

In one presently preferred embodiment, the base particles are prepared by providing inert core particles, and subsequently forming the base particles by coating the inert core particles with an inner coating composition to form an inner layer on the inert core particles. In this case, the inner coating composition preferably includes the at least one first algaecidal material.

Preferably, the inner coating composition includes a binder, with the binder preferably comprising an aluminosilicate material, preferably clay, and an alkali metal silicate. The inner coating composition can also include colorants, such as metal oxide pigments.

Preferably, the at least one first algaecidal material of the inner coating composition is selected from the group consisting of copper compounds, zinc compounds, and mixtures thereof. In one presently, preferred embodiment, the at least one first algaecidal material is cuprous oxide. In this embodiment, the cuprous oxide comprises at least about 0.5 percent of the algae-resistant granules. In another presently preferred embodiment, the at least one first algaecidal material is zinc oxide. In this embodiment, the zinc oxide comprises at least about 0.05 percent by weight of the algae-resistant granules.

In another presently preferred embodiment of the algae-resistant roofing granules of the present invention, the base particles include a metallic or metal oxide granule core, such as zinc granules or copper oxide granules. In this case, the at least one first algaecidal material is preferably selected from the group consisting of zinc, copper and copper oxide.

In yet another presently preferred embodiment, the base particles comprise microshells encapsulating the at least one first algaecidal material. Each microshell has a wall enclosing an interior cavity, and the interior cavity contains the at least one first algaecidal material. Preferably, the microshell wall is at least partially permeable to the at least one first algaecidal material.

In a presently preferred embodiment of the algae-resistant roofing granules of the present invention, the granules further comprise an interlayer between the base particle and the outer layer. The interlayer preferably enhances the release of the at least one second algaecidal material under predetermined conditions. In one aspect of the present invention, the interlayer preferably includes a water-swellable resin. Preferably, the water-swellable resin is selected from the group consisting of natural or synthetic water-swellable resins, starch, cellulose, and gums. In another aspect of the process of the present invention, the interlayer preferably includes a UV degradable material, and may optionally include a photocatalytic material. Preferably, the UV degradable polymeric material is selected from the group consisting of virgin and recycled polyolefins and polyolefin copolymers, and combinations thereof.

In a further aspect of the present invention, the at least one first algaecidal material releases algaecidal metal ions, and the interlayer includes at least one metal oxidizable by the algaecidal metal ions. Preferably, in this case the at least one first algaecidal material releases copper ions, and the interlayer includes zinc.

In a presently preferred embodiment, the at least one second algaecidal material is a quaternary ammonium compound. Preferably, the quaternary ammonium compound is selected from the group consisting of n-alkyl dimethyl benzyl ammonium chloride, dimethyl didecyl ammonium chloride, and poly(oxy-1,2-ethanediyl(dimethylimino)-1,2-ethanediyl (dimethylimino)-1,2-ethanediyl dichloride). Preferably, the organic polymeric material comprises a poly(meth)acrylate including at least one quaternary ammonium salt functional group.

In another presently preferred embodiment, the at least one second algaecidal material is an organic biocide compound. Preferably, the organic biocide can include one or more compounds that are halogen based, nitrogen based, sulfur based, or phenolics. An exemplary halogen based organic biocide is 3-iodo-2-propynylbutyl carbamate (IPBC). Oxazolidine compounds are representative of nitrogen based biocides. An exemplary sulfur based organic biocide is 2-n-octyl-4-isothiazolin-3-one (OIT). An example of a phenolic organic biocide is trichlorophenoxy phenol (TCPP).

In general, it is preferable that the outer layer have a thickness of from about 5 micrometers to about 200 micrometers; and more preferably, the outer layer has a thickness of from about 12.5 micrometers to about 40 micrometers.

The present invention also provides a sheet-roofing product, such as asphalt roof shingles or roofing membranes. In one embodiment, a sheet-roofing product according to the present invention includes a bituminous base and algae-resistant roofing granules according to the present invention.

The algae-resistant granules prepared according to the process of the present invention can be employed in the manufacture of algae-resistant roofing products, such as algae-resistant asphalt shingles or roofing membranes. The algae-resistant granules of the present invention can be mixed with conventional roofing granules, and the granule mixture can be embedded in the surface of bituminous roofing products using conventional methods. Alternatively, the algae-resistant granules of the present invention can be substituted for conventional roofing granules in manufacture of bituminous roofing products, such as asphalt roofing shingles, to provide those roofing products with algae-resistance.

It is an object of the present invention to provide a process for preparing roofing shingles to have algae-resistance that can be customized to the specific geographic region in which the shingles are intended to be used.

It is a further object of the present invention to provide algae-resistant roofing granules having controllable levels of algaecide release.

It is a further object of the present invention to provide asphalt roofing shingles resistant to algae over extended periods.

These and other objects of the invention will become apparent through the following description and claims.

DETAILED DESCRIPTION

The present invention provides algae-resistant roofing granules, algae-resistant sheet roofing products such as asphalt shingles or roofing membranes, and processes for make such products. In the present invention algae-resistance is provided by a plurality of antimicrobial agents, each of which exhibits different release rates over time. In one presently preferred embodiment, degradable boundary or containment layers are used to control the release of one or more of the biocides.

In one presently preferred embodiment, the present invention provides a process for producing time-release algae-resistant roofing granules. In this embodiment the process comprises providing base particles comprising at least one first algaecidal material, and encapsulating the base particles with an outer coating composition including at least one second algaecidal material to form an outer layer, the at least one second algaecidal material differing from the at least one first algaecidal material, the encapsulating outer layer protecting the base particles from exposure to the environment, the outer coating composition being selected such that the at least one second algaecidal material is releasable from the outer layer during a first predetermined period. Preferably, this process further comprises providing inert core particles, and forming the base particles by coating the inert core particles with an inner coating composition to form an inner layer on the inert core particles, the inner coating composition including the at least one first algaecidal material. Preferably, in this embodiment of the process of the present invention the at least one first algaecidal material is releasable from the granule during a second predetermined period. Preferably, in this embodiment, the at least one first algaecidal material is selected from the group consisting of copper compounds, zinc compounds and mixtures thereof. Preferably, in this embodiment, the outer coating composition is selected such that the outer layer fails catastrophically after a predetermined period thereby exposing the base particles to the environment.

In another presently preferred embodiment, the present invention provides time-release algae-resistant roofing granules, each granule comprising (a) a base particle comprising at least one first algaecidal material, and (b) at least one outer coating layer formed from an outer coating composition including at least one second algaecidal material and encapsulating the base particle, with the at least one second algaecidal material differing from the at least one first algaecidal material, the at least one outer layer protecting the base particle from exposure to the environment, and the outer coating composition being selected such that the at least one second algaecidal material is releasable from the outer layer during a first predetermined period. In this embodiment, it is preferred that the base particles comprise inert core particles coated with an inner coating composition to form an inner layer on the inert core particles, with the inner coating composition including the at least one first algaecidal material. Preferably, the at least one first algaecidal material is releasable from the granule during a second predetermined period. Preferably, the at least one first algaecidal material is selected from the group consisting of copper compounds, zinc compounds, and mixtures thereof. Preferably, the at least one first algaecidal material is cuprous oxide. Preferably, the outer coating composition is selected such that the outer layer fails catastrophically after a predetermined period thereby exposing the base particles to the environment.

In yet another presently preferred embodiment, the present invention provides a sheet roofing product including a bituminous base and time-release algae-resistant roofing granules. In this product, each granule comprises (a) a base particle comprising at least one first algaecidal material, and (b) at least one outer coating layer formed from an outer coating composition including at least one second algaecidal material and encapsulating the base particle, with the at least one second algaecidal material differing from the at least one first algaecidal material, the at least one outer layer protecting the base particle from exposure to the environment, and the outer coating composition being selected such that the at least one second algaecidal material is releasable from the outer layer during a first predetermined period, the at least one first algaecidal material being releasable from the granule during a second predetermined period.

Some of the presently preferred embodiments of the algae-resistant roofing granules of the present invention can be prepared through traditional granule preparation methods, such as those disclosed in U.S. Pat. No. 2,981,636, incorporated herein by reference. Other embodiments employ coating compositions including synthetic or natural organic polymeric binders.

In the algae-resistant roofing granules of the present invention, base particles are encapsulated in an outer coating that preferably fails catastrophically after an initial predetermined period. The base particles include at least one first algaecidal material, and the outer coating layer includes at least one second algaecidal material. During the initial predetermined period, algae-resistance is provided by the at least one second algaecidal material in the outer coating layer. After the initial predetermined period and the failure of the outer coating layer, algae resistance is provided by the at least one first algaecidal material of the base particles.

The base particles employed in the process of preparing the algae-resistant granules of the present invention can take several forms.

In one presently preferred embodiment, the base particles are prepared using inert core particles, which are subsequently coated with a first or inner coating composition including at least one first algaecidal material to form a first or inner layer on the core particles.

In this embodiment, the core particles are preferably chemically inert materials, such as inert mineral particles, solid or hollow glass or ceramic spheres, or foamed glass or ceramic particles. Suitable mineral particles can be produced by a series of quarrying, crushing, and screening operations, are generally intermediate between sand and gravel in size (that is, between about #8 US mesh and #70 US mesh). Preferably, the core particles have an average particle size of from about 0.2 mm to about 3 mm, and more preferably from about 0.4 mm to about 2.4 mm.

In particular, suitably sized particles of naturally occurring materials such as talc, slag, granite, silica sand, greenstone, andesite, porphyry, marble, syenite, rhyolite, diabase, greystone, quartz, slate, trap rock, basalt, and marine shells can be used, as well as recycled manufactured materials such as crushed bricks, concrete, porcelain, fire clay, and the like.

Solid and hollow glass spheres are available, for example, from Potters Industries Inc., P.O. Box 840, Valley Forge, Pa. 19482-0840, such as SPHERIGLASS® solid "A" glass spheres product grade 1922 having a mean size of 0.203 mm, product code 602578 having a mean size of 0.59 mm, BALLOTTINI impact beads product grade A with a size range of 600 to 850 micrometers (U.S. Seive size 20-30), and QCEL hollow spheres, product code 300 with a mean particle size of 0.090 mm. Glass spheres can be coated with a suitable coupling agent if desired for better adhesion to the binder of the inner coating composition.

In preparing algae-resistant roofing granules according to this embodiment of the process of the present invention, intermediate or base particles are formed by coating the inert core particles with a first or inner coating composition including at least one first algaecidal material to form at least one first or inner layer on the inert core particles, and thus to encapsulate the inert core particles. The inner coating composition includes at least one first algaecidal material, and preferably includes a suitable coating binder. The coating binder can be an inorganic or organic material, and is preferably formed from a polymeric organic material or a silicaceous material, such as a metal-silicate binder, for example an alkali metal silicate, such as sodium silicate.

When a metal-silicate binder is employed in the preparation of algae-resistant granules of the present invention, the binder preferably includes a heat-reactive aluminosilicate material, such as clay, preferably, kaolin. Alternatively, the metal silicate binder can be insolubilized chemically by reaction with an acidic material, for example, ammonium chloride, aluminum chloride, hydrochloric acid, calcium chloride, aluminum sulfate, and magnesium chloride, such as disclosed in U.S. Pat. Nos. 2,591,149, 2,614,051, 2,898,232 and 2,981, 636, each incorporated herein by reference, or other acidic material such as aluminum fluoride. In another alternative, the binder can be a controlled release sparingly water-soluble glass such as a phosphorous pentoxide glass modified with calcium fluoride, such as disclosed in U.S. Pat. No. 6,143, 318, incorporated herein by reference.

Suitable inert core particles, for example, mineral particles with size passing #8 mesh and retaining on #70 mesh, can be coated with a combination of the at least one first algaecidal material, a metal-silicate binder, kaolin clay, and, optionally, color pigments such as metal oxide pigments to reach desirable colors, followed by a heat treatment to obtain a durable inner layer or coating.

When a metal silicate binder is used, the at least one first algaecidal material is preferably selected to resist heat-induced degradation such as that encountered during elevated temperature cure of the metal silicate binder. Thus, in this case, the at least one first algaecidal material is preferably an inorganic algaecidal material, such as cuprous oxide, zinc oxide, or the like. Conversely, when, for example, a polymeric organic material is employed as a binder for the inner layer coating composition, such as a polymeric (meth)acrylate, an epoxide, or the like, which does not require an elevated temperature cure, the at least one first algaecidal material can be an organic algaecidal material.

When the coated core particles are fired at an elevated temperature, such as at least about 400 degrees C., and preferably at about 500 to about 650 degrees C., the clay binder densifies to form strong particles.

Examples of clays that can be employed in the process of the present invention include kaolin, other aluminosilicate clays, Dover clay, bentonite clay, etc.

In the alternative, a suitable siliceous binder can be formed from sodium silicate, modified by the addition of at least one of sodium fluorosilicate, aluminum fluoride, or Portland cement.

Preferably, the at least one first algaecidal material of the inner coating composition is selected from the group consisting of copper compounds, zinc compounds, and mixtures thereof. In one presently preferred embodiment, the at least one first algaecidal material is cuprous oxide. In this embodiment, the cuprous oxide comprises at least 0.5 percent of the algae-resistant granules. In another presently preferred embodiment, the at least one first algaecidal material is zinc oxide. In this embodiment, the zinc oxide comprises at least 0.05 percent by weight of the algae-resistant granules.

In another presently preferred embodiment of the algae-resistant roofing granules of the present invention, the base particles include a metallic or metal oxide granule core, such as zinc granules or copper oxide granules. In this case, the at least one first algaecidal material is preferably selected from the group consisting of zinc, copper and copper oxide.

In yet another presently preferred embodiment, the base particles comprise microshells encapsulating the at least one first algaecidal material. Each microshell has a wall enclosing an interior cavity, and the interior cavity contains the at least one first algaecidal material. Preferably, the microshell wall is at least partially permeable to the at least one first algaecidal material.

Microshells for use in the present invention can be prepared from inorganic materials such as glass and ceramic materials such as silica-alumina ceramics, or from synthetic polymeric materials such as poly(meth)acrylates, epoxy resins, polyurethanes, polypropylene, polyimides, acrylonitrile copolymers, vinylidene halide copolymers, and the like. The production of large (up to 6 mm), porous hollow glass microshells is disclosed, for example, in U.S. Pat. Nos. 5,225, 123 and 5,397,759, each incorporated herein by reference.

The at least one first algaecidal material can be encapsulated in microshells using conventional techniques for forming microcapsules or microshells, including such techniques as interfacial polymerization, phase separation/coacervation, spray drying, spray coating, fluid bed coating, supercritical anti-solvent precipitation, and the like. Techniques for microencapsulating solid biocidal particles and other solid particles are disclosed, for example, in G. Beestman, "Microencapsulation of Solid Particles," *Controlled-Release Delivery Systems for Pesticides*, (H. B. Scher, Ed., Marcel Dekker, Inc. New York 1999) pp. 31-54, Kirk-Othmer Encyclopedia of Chemical Technology, 4th Edition; as well in U.S.

Pat. Nos. 6,156,245, 6,797,277, and 6,861,145. Preferably, the microshells formed have an average size of from about 200 micrometers to about 5 millimeters, and more preferably of from about 250 micrometers to about 3.2 millimeters, and even more preferably of from about 400 to about 2.5 millimeters. Preferably, when a synthetic polymeric material is employed to form microshell walls, a material with good exterior durability such as a poly(meth)acrylate is selected.

Preferably, the microshells are formulated to provide controlled release of the at least one first algaecidal material from the microshells over an extended period. A mixture of microshells having differing time-release characteristics can be employed, so that there is a continuous release of the at least one algaecidal material over an extended period of time.

The microshell wall is formed such that the at least one first algaecidal material encapsulated within the microshell can diffuse through the wall when the exterior of the wall is exposed to the environment. The rate of release of the at least one first algaecidal material depends on a number of factors, including the nature of the at least one algaecidal material, the nature of the material from which the microshell wall is formed, the thickness of the microshell wall, the geometry and size of the microshell, specific morphological features of the microshell wall such as the existence, distribution, and characteristics of pores in the wall, etc.

Preferably, the microcapsules are formed from a material that provides capsule walls that are environmentally degradable in a controlled manner. Such controlled release microcapsules are well known in the pharmaceutical and agrochemical arts. A variety of mechanisms can be employed to provide such capsules. For example, the capsule wall can include additive to increase their sensitivity to environmental degradation, such as disclosed in U.S. Pat. No. 6,936,644 (IR sensitivity).

The outer coating composition includes the at least one second algaecidal material that provides algae resistance during the initial predetermined period. In the various embodiments of the present invention, the outer coating composition forms an outer layer that encapsulates, directly or indirectly, the base particles as prepared according to each of the various alternative embodiments described above. Preferably, the outer coating composition includes a binder. Preferably, the composition and/or morphology of the encapsulating outer layer are selected such that the encapsulating outer layer fails after a predetermined time to expose the first layer to the environment. For example, the outer coating composition can comprise a mixture of compatible polymeric materials with differing proportions of hydrophilic functional groups such that one of the polymeric materials is water sensitive and the other or second polymeric material has substantially less water sensitivity than the first polymeric material. The proportions of hydrophilic residues in the two polymeric materials and the weight ratio of the two polymeric materials are preferably selected such that during the predetermined period, environmental water gradually diffuses into and through the outer coating layer to swell the first polymeric material, eventually causing the layer to fail catastrophically.

For example, the two polymeric materials can each be a copolymer of (meth)acrylate monomers, including hydrophobic monomer such as n-butyl acrylate, ethyl acrylate and methyl methacrylate, and hydrophilic monomers such as hydroxyethyl methacrylate, methacrylic acid and acrylic acid, with the molar ratio of hydrophobic monomer to hydrophilic monomer in the first polymeric material from that of the second polymeric material.

In another, alternative embodiment, the outer coating composition includes an incompatible mixture of polymeric materials with differing proportions of hydrophilic functional groups such that one of the polymeric materials is water sensitive and the other or second polymeric material has substantially less water sensitivity than the first polymeric material, and the two polymeric material tend to form separate phases. The weight ratio of the two polymeric materials is preferably selected such that during the predetermined period, environmental water gradually diffuses into and through the outer coating layer to swell the first polymeric material in one of the two phases, eventually causing the entire layer to fail catastrophically. In yet another alternative embodiment, the outer coating composition includes an incompatible mixture of polymeric materials with differing proportions of hydrophilic functional groups such that one of the polymeric materials is water sensitive and the other or second polymeric material has substantially less water sensitivity than the first polymeric material, and the two polymeric material tend to form separate phases, but the two polymeric material are crosslinked together to form an interpenetrating polymer network. Again, the proportions of hydrophilic functional groups and the weight ratio of the two polymeric materials are preferably selected such that during the predetermined period, environmental water gradually diffuses into and through the outer coating layer to swell the first polymeric material eventually causing the outer layer to fail catastrophically.

Thus, in one presently preferred embodiment, the binder of the outer coating composition comprises an organic polymeric material, and the organic polymeric material is preferably selected from the group consisting of poly(meth)acrylates. The at least one second algaecidal material is preferably initially uniformly dispersed in the organic polymeric material. The second algaecidal material subsequently diffuses to the exterior surface of the outer layer and is released into the environment to provide algae resistance.

In another presently preferred embodiment of the present invention, an interlayer is provided between the core particle and the outer layer. The interlayer preferably enhances the release of the at least one first algaecidal material by failing catastrophically after a predetermined period. For example, the interlayer can be formed by a hydrophilic, water-swellable polymeric material. During the predetermined period, water can diffuse through the outer layer, which preferably has a composition such that the outer layer is substantially hydrophobic and only slightly water permeable. Eventually, however, enough water diffuses through the outer layer to cause the interlayer to swell significantly, disrupting the outer layer and causing the outer layer to fail catastrophically. Preferably, interlayer comprises at least one water-swellable resin selected from the group consisting of natural or synthetic water-swellable resins, starch, cellulose, and gums.

In another presently preferred embodiment of the present invention, an interlayer is provided between the core particle and the outer layer including a UV degradable material. The interlayer preferably enhances the release of the at least one first algaecidal material by failing catastrophically after a predetermined period. For example, the interlayer can be formed by UV degradable polymeric material, and may optionally include a photocatalytic material, as needed. During the predetermined period, UV light transmission through the outer layer can cause photochemical degradation of the interlayer. Eventually, however, enough degradation takes place in the interlayer leading to disrupting of the outer layer and causing the outer layer to fail catastrophically. Preferably, interlayer comprises at least one UV degradable material selected from the group of virgin and recycled polyolefins and polyolefin copolymers, and combinations thereof. Exemplary photocatalytic materials include oxides of titanium and zinc.

In other aspect of the process of the present invention, the at least one first algaecidal material releases algaecidal metal ions, and the interlayer includes at least one metal oxidizable or corrodible by the algaecidal metal ions. In this case, the interlayer gradually becomes more hydrophilic and swellable over time as the metal oxidizable by the at least one first algaecidal material becomes oxidized, eventually failing catastrophically to disrupt the outer layer and expose the base particles to the environment. Preferably, in this case the at least one first algaecidal material releases copper ions, and the interlayer includes zinc.

The at least one first algaecidal material and the at least one second algaecidal material can be identical, or they can differ from one another. The at least one first algaecidal material and the at least one second algaecidal material can be selected from inorganic biocidal materials, such as copper, cuprous oxide, cupric acetate, cupric chloride, cupric nitrate, cupric oxide, cupric sulfate, cupric sulfide, cupric stearate, cupric cyanide, cuprous cyanide, cuprous stannate, cuprous thiocyanate, cupric silicate, cuprous chloride, cupric iodide, cupric bromide, cupric carbonate, cupric fluoroborate, zinc oxide, such as French process zinc oxide, zinc sulfide, zinc borate, zinc sulfate, zinc pyrithione, zinc ricinoleate, zinc stearate, zinc chromate, zinc carbonate, titanium oxide (such as the photocatalytic anatase), metallic silver, silver oxide, silver chloride, silver bromide, silver iodide and mixtures thereof. Metal alloys, such as alloys of copper and silver, alloys of copper and zinc, and alloys of silver and zinc, can also be employed.

The proportion of algaecidal materials in the algae-resistant roofing granules can be adjusted depending on a number of factors, such as the intended use of the roofing products manufactured using the algae-resistant granules, the expected environmental conditions at the site where the roofing products including the algae-resistant granules are to be installed, the proportion of algaecidal materials in the algae-resistant granules, the proportion of algae-resistant roofing granules to conventional non-algae-resistant roofing granules employed in the roofing product, et al. In general, however, the proportion of algaecidal materials is preferably selected to provide algae-resistant roofing granules in which the algaecidal material comprises from about 0.005 to about 10 percent by weight of the granules. Preferably, the proportion of algaecidal material in the exterior coating composition is selected to provide algae-resistant roofing granules in which the biocidal particles have a surface area of from about 0.05 to about 5 square meter per gram of algae-resistant roofing granules.

The algae resistance properties of the algae-resistant roofing granules of the present invention are determined by a number of factors, including the porosity of the surface coating of the roofing granules, the nature and amount(s) of the algaecidal materials employed, and the spatial distribution of the algaecidal materials in the granules.

The algae-resistant roofing granules of the present invention can be colored using conventional coatings pigments. The coatings pigments can be included in the outer layer, in the inner layer (in those embodiments of the present invention that employ an inner coating layer), or both the inner layer and the outer layer. Examples of coatings pigments that can be used include those provided by the Color Division of Ferro Corporation, 4150 East 56th St., Cleveland, Ohio 44101, and produced using high temperature calcinations, including PC-9415 Yellow, PC-9416 Yellow, PC-9158 Autumn Gold, PC-9189 Bright Golden Yellow, V-9186 Iron-Free Chestnut Brown, V-780 Black, V0797 IR Black, V-9248 Blue, PC-9250 Bright Blue, PC-5686 Turquoise, V-13810 Red, V-12600 Camouflage Green, V12560 IR Green, V-778 IR Black, and V-799 Black. The said roofing granules can also contain color pigments or additives that reflect solar radiation. Preferably, the color pigments or additives can reflect the near infrared radiations of solar spectrum, such that the solar heat absorption can be reduced without affecting the color.

The process of the present invention advantageously permits the algae resistance of the shingles employing the algae-resistant granules to be tailored to specific local conditions. For example, in geographic areas encumbered with excessive moisture favoring rapid algae growth, the granules can be structured to release the relatively high levels of algaecide required to effectively inhibit algae growth under these conditions. Conversely, where algae growth is less favored by local conditions, the granules can be structured to release the lower levels of algaecide effective under these conditions.

Referring now to the drawings, in which like reference numerals refer to like elements in each of the several views, there are shown schematically in FIGS. 1, 2, 3 and 4 examples of algae-resistant granules prepared according to the process of the present invention.

Figure 1:
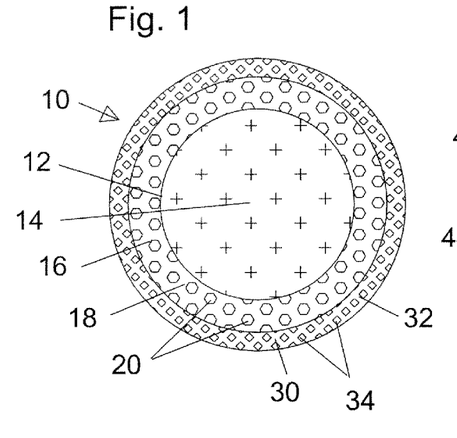
FIG. 1 is a schematic representation of a first type of an algae-resistant granule of the present invention.

FIG. 1 is a schematic representation of a first type of an algae-resistant granule of the present invention. FIG. 1 schematically illustrates an algae-resistant granule 10 formed from a base particle 12 comprising an inert mineral core particle 14 covered with an inner layer 16 composed of an inner coating composition 18 including a first algaecidal material 20. The base particle 12 is in turn covered with an outer coating layer 30 comprising an outer coating composition 32 including a second algaecidal material 34.

Figure 2:
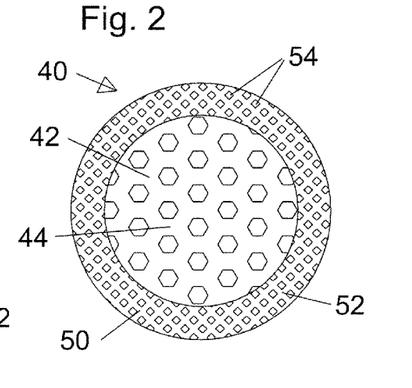
FIG. 2 is a schematic representation of a second type of an algae-resistant granule of the present invention.

FIG. 2 is a schematic representation of a second type of an algae-resistant granule of the present invention. FIG. 2 schematically illustrates an algae-resistant granule 40 formed from a base particle 42 comprising a metallic granule core 44 of a first algaecidal material. The base particle 42 is covered with an outer coating layer 50 comprising an outer coating composition 52 including a second algaecidal material 54.

Figure 3:
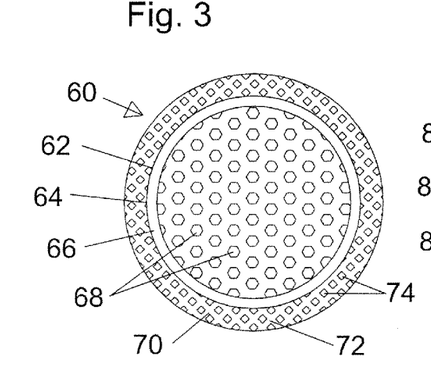
FIG. 3 is a schematic representation of a third type of an algae-resistant granule of the present invention.

FIG. 3 is a schematic representation of a third type of an algae-resistant granule of the present invention. FIG. 3 schematically illustrates an algae-resistant granule 60 formed from a base particle 62 comprising a microshell 64 having an exterior wall 66 encapsulating a first algaecidal material 68. The base particle 62 is in turn covered with an outer coating layer 70 comprising an outer coating composition 72 including a second algaecidal material 74.

Figure 4:
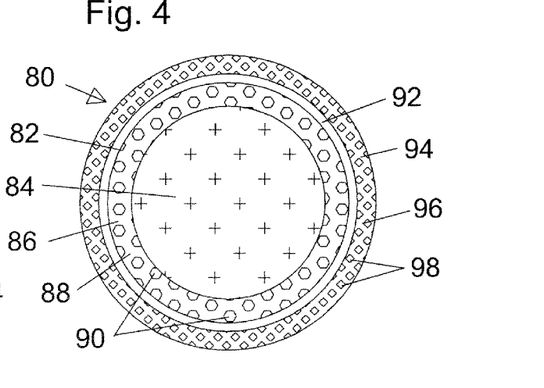
FIG. 4 is a schematic representation of a fourth type of an algae-resistant granule of the present invention.

FIG. 4 is a schematic representation of a fourth type of an algae-resistant granule of the present invention. FIG. 4 schematically illustrates an algae-resistant granule 80 formed from a base particle 82 comprising an inert mineral core particle 84 covered with an inner layer 86 composed of a inner coating composition 88 including a first algaecidal material 90. The base particle 82 is in turn covered with an interlayer 92 formed from a material that is selected to fail catastrophically after a predetermined period. The interlayer 92 is in turn covered with an outer coating layer 94 comprising an outer coating composition 96 including a second algaecidal material 98.

Figure 5:
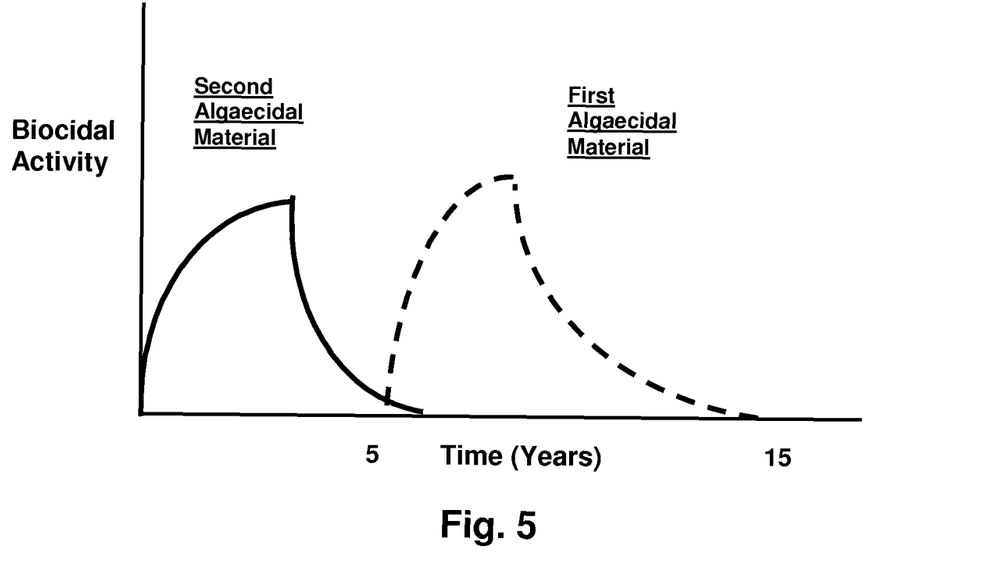
FIG. 5 is a schematic representation graphing the release of algaecide from algae-resistant granules of the present invention as a function of time.

FIG. 5 is a schematic graphical representation showing the release of algaecidal material over time from an algae-resistant granule according to the present invention. In this example, conventional cuprous oxide-loaded algae resistant granules are encapsulated with an acrylic coating including an algaecidal quaternary ammonium salt. Initially, algae resistance is provided by the release of the second algaecidal material, such as a quaternary ammonium salt, from the outer layer of the granule. The acrylic coating is formulated to last for five years. During this time, the ammonium salt functions as the sole biocide to prevent algae growth. After the predetermined period, the outer layer fails catastrophically, so that portions of the surface of the base particle are exposed to the environment. At the end of five years, numerous cracks start forming on the coating surface due to weathering. Soon afterward, the film peels off from the algae resistant granules, or otherwise loses film integrity. The granules are now exposed to the environment, and cuprous oxide embedded on the granule surfaces starts leaching out and becomes the sole biocide, which is effective for an additional ten years. From the time the outer coating is lost, algae resistance is provided by the first algaecidal material, namely, the cuprous oxide. The result is an algae-resistant system that is effective against algae for fifteen years.

The present invention also provides a process for the manufacture of algae-resistant roofing granules. The process comprises providing base particles comprising at least one first algaecidal material. The base particles can be prepared in a number of different ways. The base particles are in turn encapsulated with an outer coating composition including at least one second algaecidal material to form an outer layer. The at least one second algaecidal material preferably differs from the at least one first algaecidal material. The encapsulating outer layer protects the base particles from exposure to the environment. The outer coating composition is preferably selected such that the outer layer fails catastrophically after a predetermined period thereby exposing the base particles to the environment.

In one presently preferred embodiment, the base particles are prepared by providing inert core particles, and subsequently forming the base particles by coating the inert core particles with an inner coating composition to form an inner layer on the inert core particles. In this case, the inner coating composition preferably includes the at least one first algaecidal material.

Preferably, the inner coating composition includes a binder, which preferably comprises an aluminosilicate material, such as clay, and an alkali metal silicate. The inner coating composition can also include colorants, such as metal oxide pigments, and other components, such as solar heat-reflective pigments.

In the present process, the at least one first algaecidal material of the inner coating composition is preferably selected from the group consisting of copper compounds, zinc compounds, and mixtures thereof, with cuprous oxide and zinc oxide being especially preferred. When cuprous oxide is employed as the at least one first algaecidal material, the cuprous oxide preferably comprises at least 0.5 percent of the algae-resistant granules. When zinc oxide is employed as the at least one first algaecidal material, the zinc oxide preferably comprises at least 0.05 percent by weight of the algae-resistant granules.

In another presently preferred embodiment of the present process, the base particles are prepared by providing a metallic or metal oxide granule core, such as zinc granules or copper oxide granules. In this case, the at least one first algaecidal material is preferably selected from the group consisting of zinc, copper and copper oxide.

In another presently preferred embodiment of the present process, the base particles are prepared by providing the at least one first algaecidal material, and forming the base particles by encapsulating the at least one first algaecidal material in microshells. Each microshell has a wall enclosing an interior cavity, and the interior cavity contains the at least one first algaecidal material. Preferably, the microshell wall is at least partially permeable to the at least one first algaecidal material.

In a presently preferred embodiment of the process of the present invention, the process further comprises providing an interlayer on the base particles. The interlayer preferably enhances the release of the at least one second algaecidal material under predetermined conditions. In one aspect of the process of the present invention, the interlayer preferably includes a water-swellable resin or a UV degradable material. Preferably, the water-swellable resin is selected from the group consisting of natural or synthetic water-swellable resins, starch, cellulose, and gums. Preferred UV degradable materials include virgin or recycled polyolefins, virgin or recycled olefin copolymers, and mixtures or combinations thereof. In other aspect of the process of the present invention, the at least one first algaecidal material releases algaecidal metal ions, and the interlayer includes at least one metal oxidizable by the algaecidal metal ions. Preferably, in this case the at least one first algaecidal material releases copper ions, and the interlayer includes zinc.

Preferably, in the present process, the outer coating composition includes a binder. Preferably, the composition and/or morphology of the encapsulating outer layer are selected such that the encapsulating outer layer fails after a predetermined time to expose the first layer to the environment. Thus, the second algaecide is released from the outer layer during the initial predetermined period.

In one presently preferred embodiment, the binder of the outer coating composition comprises an organic polymeric material or an inorganic material. The organic polymeric material is preferably selected from the group consisting of poly(meth)acrylates, polyurethanes and polyureas. When an inorganic material is used as the binder, the inorganic material is preferably selected from the group consisting of an aluminosilicate, silica and phosphate materials. In the process of the present invention, the at least one second algaecidal material is preferably initially uniformly dispersed in the binder. The second algaecidal material subsequently diffuses to the exterior surface of the outer layer and is released into the environment.

In a presently preferred embodiment, the at least one second algaecidal material is a quaternary ammonium compound. Preferably, the organic biocides include compounds that are halogenated based (such as IPBC [3-iodo-2-propynylbutyl carbamate]), nitrogen based (such as oxazolidines), sulfur based (such as OIT [2-n-octyl-4-isothiazolin-3-one]), or phenolics (such as TCPP [trichlorophenoxy phenol]). Preferably, the quaternary ammonium compound is selected from the group consisting of n-alkyl dimethyl benzyl ammonium chloride, dimethyl didecyl ammonium chloride, and poly (oxy-1,2-ethanediyl(dimethylimino)-1,2-ethanediyl(dimethylimino)-1,2-ethanediyl dichloride). Preferably, the binder is an organic polymeric material including at least one quaternary ammonium salt functional group. More preferably, the organic polymeric material is a poly(meth)acrylate.

In another presently preferred embodiment, the at least one second algaecidal material is an organic biocide. Preferably, the organic biocide includes one or more compounds that are halogenated, such as 3-iodo-2-propynylbutyl carbamate (IPBC), nitrogen based, such as oxazolidines, sulfur based, such as 2-n-octyl-4-isothiazolin-3-one (OIT), or phenolic in nature, such as trichlorophenoxy phenol (TCPP).

The coating compositions used in preparing the algae-resistant granules can include other components, such as conventional metal oxide colorants of the type employed in the manufacture of roofing granules, solar heat-reflective pigments such as titanium dioxide, other biocidal materials, and the like.

The algae-resistant granules prepared according to the process of the present invention can be employed in the manufacture of algae-resistant roofing products, such as algae-resistant asphalt shingles, using conventional roofing production processes. Typically, bituminous roofing products are sheet goods that include a non-woven base or scrim formed of a fibrous material, such as a glass fiber mat. The base is coated with one or more layers of a bituminous material such as asphalt to provide water and weather resistance to the roofing product. One side of the roofing product is typically coated with mineral granules to provide durability, reflect heat and solar radiation, and to protect the bituminous binder from environmental degradation. The algae-resistant granules of the present invention can be mixed with conventional roofing granules, and the granule mixture can be embedded in the surface of such bituminous roofing products using conventional methods. Alternatively, the algae-resistant granules of the present invention can be substituted for conventional roofing granules in the manufacture of bituminous roofing products to provide those roofing products with algae-resistance.

Bituminous roofing products are typically manufactured in continuous processes in which a continuous substrate sheet of a fibrous material such as a continuous felt sheet or glass fiber mat is immersed in a bath of hot, fluid bituminous coating material so that the bituminous material saturates the substrate sheet and coats at least one side of the substrate. The reverse side of the substrate sheet can be coated with an anti-stick material such as a suitable mineral powder or a fine sand. Roofing granules are then distributed over selected portions of the top of the sheet, and the bituminous material serves as an adhesive to bind the roofing granules to the sheet when the bituminous material has cooled. The sheet can then be cut into conventional shingle sizes and shapes (such as one foot by three feet rectangles), slots can be cut in the shingles to provide a plurality of "tabs" for ease of installation, additional bituminous adhesive can be applied in strategic locations and covered with release paper to provide for securing successive courses of shingles during roof installation, and the finished shingles can be packaged. More complex methods of shingle construction can also be employed, such as building up multiple layers of sheet in selected portions of the shingle to provide an enhanced visual appearance, or to simulate other types of roofing products.

The bituminous material used in manufacturing roofing products according to the present invention is derived from a petroleum processing by-product such as pitch, "straight-run" bitumen, or "blown" bitumen. The bituminous material can be modified with extender materials such as oils, petroleum extracts, and/or petroleum residues. The bituminous material can include various modifying ingredients such as polymeric materials, such as SBS (styrene-butadiene-styrene) block copolymers, resins, oils, flame-retardant materials, oils, stabilizing materials, anti-static compounds, and the like. Preferably, the total amount by weight of such modifying ingredients is not more than about 15 percent of the total weight of the bituminous material. The bituminous material can also include amorphous polyolefins, up to about 25 percent by weight. Examples of suitable amorphous polyolefins include atactic polypropylene, ethylene-propylene rubber, etc. Preferably, the amorphous polyolefins employed have a softening point of from about 130 degrees C. to about 160 degrees C. The bituminous composition can also include a suitable filler, such as calcium carbonate, talc, carbon black, stone dust, or fly ash, preferably in an amount from about 10 percent to 70 percent by weight of the bituminous composite material.

The following examples are provided to better disclose and teach processes and compositions of the present invention. They are for illustrative purposes only, and it must be acknowledged that minor variations and changes can be made without materially affecting the spirit and scope of the invention as recited in the claims that follow.

Example 1

Preparation of Encapsulated AR Granules 1,000 g of conventional cuprous oxide-loaded algae-resistant (AR) roofing granules (Product Code GH 71 AR) manufactured at CertainTeed's Gads Hill roofing granule plant located at Piedmont, Mo. were used as the base particles. In this case, cuprous oxide acted as the first algaecidal material. These granules were in turn encapsulated with an outer coating. Composition of this outer coating consisted of 125 g of sodium silicate (40% solids, with $Na_2O:SiO_2$ ratio of 1:3.2; Occidental Chemical Corporation, Dallas, Tex.), 100 g of clay slurry (70% solids, Unimin Corporation, New Canaan, Conn.), 20 g of titanium oxide (TiPure Product Number R-101, DuPont, Wilmington, Del.) and 120 g of water. The outer coating was applied onto the roofing granules using a fluidized bed coater Model 2 supplied by Fluid Air, Inc. (Aurora, Ill.). The operating conditions were set at 24 scfm of inlet air flow rate, 70° C. of inlet temperature, 10 psi of spraying pressure, 65 psi of filter blow back pressure, 5.3 g/min of binder solution pump rate, and total processing time of 40 minutes. The coated granules were then fired in a gas-fired kiln at a temperature of 500° C. for 20 minutes to form a composite roofing granule having cuprous oxide in the interior fully encapsulated by an exterior layer of sodium silicate binder.

Example 2

Preparation of Encapsulated AR Granules

The process of Example 1 was repeated, except the outer coating composition was modified. The composition consisted of 188 g of sodium silicate (40% solids, with $Na_2O:SiO_2$ ratio of 1:3.2; Occidental Chemical Corporation, Dallas, Tex.), 100 g of clay slurry (70% solids, Unimin Corporation, New Canaan, Conn.), 20 g of titanium oxide (TiPure Product Number R-101, DuPont, Wilmington, Del.), 12 g of zinc oxide (Zinc Corporation of America, Monaca, Pa.) and 150 g of water. The coated granules were fired in a gas-fired kiln at a temperature of 500° C. for 20 minutes to form a composite roofing granule having cuprous oxide in the interior fully encapsulated by an exterior layer of zinc oxide-loaded sodium silicate binder. In this case, the resultant composite granules have dual algaecides: cuprous oxide in the interior and zinc oxide on the outer layer.

Example 3

Preparation of Encapsulated AR Granules

The process of Example 1 was repeated, except the outer coating composition was modified further. The composition consisted of 60 g of colloidal silica Ludox CL-X (45% solids, pH 9.1, Sigma-Aldrich Corporation, St. Louis, Mo.), 30 g of clay slurry (70% solids, Unimin Corporation, New Canaan, Conn.), 12 g of aluminum phosphate (Sigma-Aldrich Corporation, St. Louis, Mo.), 20 g of titanium oxide (TiPure R-101, DuPont, Wilmington, Del.), 18 g of zinc oxide (Zinc Corporation of America, Monaca, Pa.) and 135 g of water. The coated granules were fired in a gas-fired kiln at a temperature of 500° C. for 20 minutes to form a composite roofing granule having cuprous oxide on the interior fully encapsulated by an exterior layer of zinc oxide-loaded phosphate binder. In this case, the resultant composite granules have dual algaecides: cuprous oxide in the interior and zinc oxide on the outer layer.

Leaching Procedure of Metal Ions from Roofing Granules

Leaching study was conducted on roofing granules which were immersed in warm water at pH 5 and 45° C. The reported leached concentration of metal ions, in ppm, is the amount of ions leached out to the environment. The leaching procedure was as follows:

10 g of the test granules were placed in a clean 40 ml glass vial filled with 10 ml of pH 5.0 buffer (potassium biphthalate-sodium hydroxide buffer, 0.05M, Fisher Scientific). The vial was placed in a water bath (Fisher Scientific ISOTEMP Model 220) and maintained at a constant temperature of 45° C. After one day, the solution was decanted into a cuvette, and a pre-measured packet of powder pillow containing a coloring reagent was added to the solution. Selection of the coloring agent depended on the metal ions to be measured. For the detection of copper ions, CuVer 1 copper reagent of dipotassium 2,2' bicinchoninate (Product number 21058-69, Hach Company, Loveland, Colo.) was used. The concentration of copper ions, in ppm, leached out from the granules into the surrounding water was determined by measuring the color intensity of the resulted complex at 560 nm using a laboratory spectrophotometer (Model DR/2010 by Hach Company).

Figure 6:
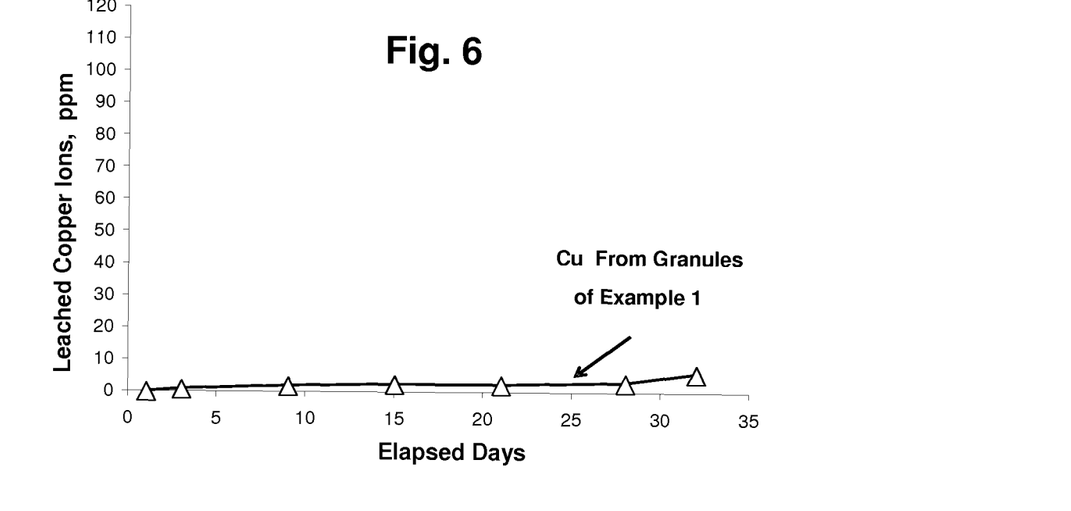
FIG. 6 is a graph showing the release of copper ions as a function of time from algae-resistant granules according to the present invention prepared according to Example 1.

For the detection of zinc ions, Zinc VerS reagent containing potassium borate, boron oxide, sodium ascorbate and potassium cyanide (Product number 21066-69, Hach Company) was used. The concentration of zinc ions, in ppm, leached out from the granules into the surrounding water was determined by measuring the color intensity of the resulted complex at 620 nm using a laboratory spectrophotometer (Model DR/2010 by Hach Company). The composite granules prepared following the procedure described in Example 1 consist of cuprous oxide, from the conventional AR roofing granules, in the interior. Using the fluidized bed coating process, these AR granules were in turn coated with an outer layer of sodium silicate binder. The AR granules were well encapsulated by the sodium silicate binder so that only very minimal amount of copper ions was able to escape through the outer layer and leach out to the surrounding. FIG. 6 shows that the leaching of copper ions started at very low level (below 0.5 ppm), and reached around 5 ppm after one month.

The composite granules prepared following the procedure described in Example 1 consist of cuprous oxide, from the conventional AR roofing granules, in the interior. Using the fluidized bed coating process, these AR granules were in turn coated with an outer layer of sodium silicate binder. The AR granules were well encapsulated by the sodium silicate binder so that only very minimal amount of copper ions was able to escape through the outer layer and leach out to the surrounding. FIG. 6 shows that the leaching of copper ions started at very low level (below 0.5 ppm), and reached around 5 ppm after one month.

Figure 7:
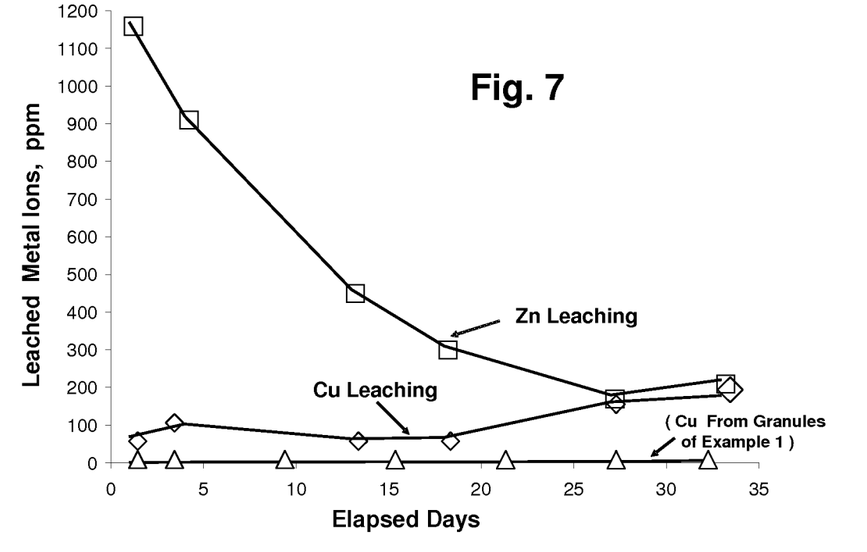
FIG. 7 is a graph showing the release of copper ions as a function of time from algae-resistant granules according to the present invention prepared according to Example 2.

For the composite granules prepared following the procedure described in Example 2, the outer layer of sodium silicate binder encapsulating the AR granules was not able to prevent copper ions from leaching out to the surroundings. The leached copper concentration was 57 ppm on the first day, and increased to 167 ppm after one month. In addition, the outer layer contained zinc oxide as the second algaecide, which was leached out rapidly and reduced to less than 20% of its initial concentration after one month. The leaching curves of copper and zinc ions from granules of Example 2 are depicted FIG. 7, in comparison to the leaching of copper ions from the granules of Example 1.

Figure 8:
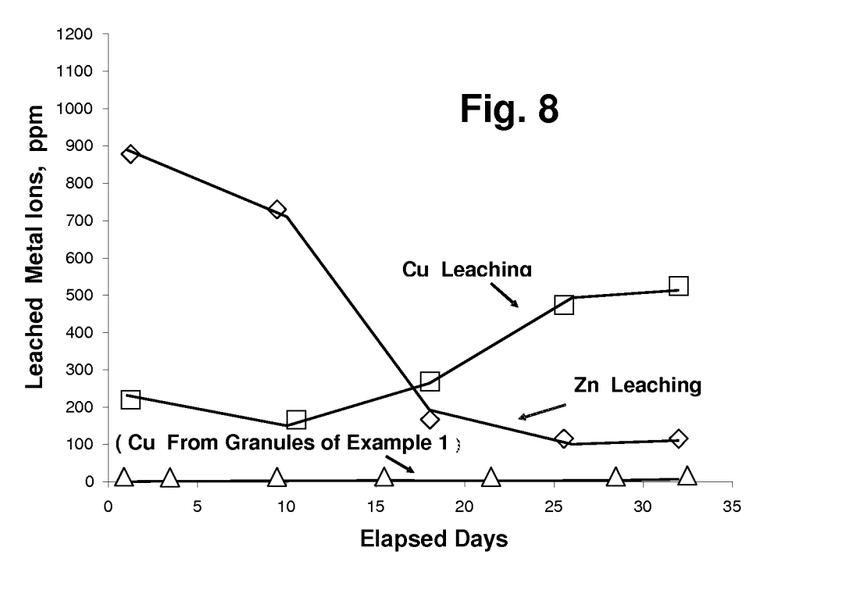
FIG. 8 is a graph showing the release of copper ions as a function of time from algae-resistant granules according to the present invention prepared according to Example 3.

Composite granules prepared per Example 3 had a different material composition for the outer layer. A metal phosphate binder was used in place of the silicate binder as in Example 2. The initial leached copper level was even higher at 232 ppm, then increased rapidly to 513 ppm after one month. While the leaching of copper ions from these granules was more accelerated than that of the granules from Example 2, the leaching of zinc ions as the second algaecide from both cases was rather similar, as can be seen in FIG. 8.

These results demonstrate that by proper design and selection of the material and composition of the outer layer, and of the base particle, the leaching rate and concentration of the algaecide from the interior can be controlled at will. Furthermore, a second algaecide can be added to the outer layer, if desired, for specific functionalities, and the leaching of the second algaecide can also be modified accordingly.

Various modifications can be made in the details of the various embodiments of the processes, compositions and articles of the present invention, all within the scope and spirit of the invention and defined by the appended claims.

We claim:

1. A process for producing time-release algae-resistant roofing granules, the process comprising:
    (a) providing base particles comprising at least one first algaecidal material;
    (b) providing an interlayer on the base particles, the interlayer enhancing the release of the at least one first algaecidal material under predetermined conditions, and
    (c) encapsulating the interlayer-covered base particles with an outer coating composition including at least one second algaecidal material to form an outer layer, the at least one second algaecidal material differing from the at least one first algaecidal material, the encapsulating outer layer protecting the base particles from exposure to the environment, the at least one second algaecidal material being releasable from the outer layer during a predetermined period.

2. A process according to claim 1 further comprising;
    (a) providing inert core particles; and
    (b) forming the base particles by coating the inert core particles with an inner coating composition to form an inner layer on the inert core particles, the inner coating composition including the at least one first algaecidal material.

3. A process according to claim 2 wherein the inner coating composition includes a binder comprising an aluminosilicate material and an alkali metal silicate.

4. A process according to claim 1 wherein the at least one first algaecidal material is selected from the group consisting of copper compounds, zinc compounds, and mixtures thereof.

5. A process according to claim 1 wherein the outer coating composition includes a binder comprising a material selected from the group consisting of an organic polymeric material or/and an inorganic material.

6. A process according to claim 1 further comprising providing base particles comprising metallic granules.

7. A process according to claim 1 wherein the interlayer includes a UV degradable material selected from the group consisting of virgin and recycled natural or synthetic polymers and copolymers and combinations thereof.

8. A process according to claim 1 wherein the interlayer includes a photocatalytic material.

9. Time-release algae-resistant roofing granules, each granule comprising:
(a) a base particle comprising at least one first algaecidal material; and
(b) an interlayer formed on the base particles, the interlayer enhancing the release of the at least one first algaecidal material under predetermined conditions, and
(c) at least one outer coating layer formed from an outer coating composition including at least one second algaecidal material and encapsulating the base particle, the at least one second algaecidal material differing from the at least one first algaecidal material, the encapsulating at least one outer layer protecting the base particle from exposure to the environment, the at least one second algaecidal material being releasable from the outer layer during a predetermined period.

10. Time-release algae-resistant roofing granules according to claim 9 wherein the base particles comprise inert core particles coated with an inner coating composition to form an inner layer on the inert core particles, the inner coating composition including the at least one first algaecidal material.

11. Time-release algae-resistant roofing granules according to claim 9 wherein the at least one first algaecidal material is releasable from the granule during a second predetermined period.

12. Time-release algae-resistant roofing granules according to claim 9 wherein the inner coating composition includes a binder comprising an aluminosilicate material and an alkali metal silicate.

13. Time-release algae-resistant roofing granules according to claim 9 wherein the at least one first algaecidal material is selected from the group consisting of copper compounds, zinc compounds, and mixtures thereof.

14. Time-release algae-resistant roofing granules according to claim 13 wherein the at least one first algaecidal material is cuprous oxide.

15. Time-release algae-resistant roofing granules according to claim 9 wherein the outer coating composition includes a binder comprising a material selected from the group consisting of an organic polymeric material and an inorganic material.

16. Time-release algae-resistant roofing granules according to claim 15 wherein the at least one second algaecidal material is initially uniformly dispersed in the binder, and subsequently diffuses to the exterior surface of the outer layer.

17. Time-release algae-resistant roofing granules according to claim 9 wherein the at least one second algaecidal material is an organic biocide.

18. Time-release algae-resistant roofing granules according to claim 17 wherein the binder is selected from the group consisting of poly(meth)acrylate, polyurethanes and polyureas and the inorganic materials include aluminosilicate, silica and phosphate binders.

19. Time-release algae-resistant roofing granules according to claim 9 wherein the outer layer has a thickness of from about 5 micrometers to about 200 micrometers.

20. Time-release algae-resistant roofing granules according to claim 9 wherein the base particles comprise metallic granules.

* * * * *